(12) United States Patent
Nido

(10) Patent No.: US 12,077,780 B2
(45) Date of Patent: Sep. 3, 2024

(54) CONDITIONED MEDIUM FROM CELLS CULTURED UNDER HYPOXIC CONDITIONS AND USES THEREOF

(71) Applicant: Allergan Sales, LLC, Irvine, CA (US)

(72) Inventor: Patrick Nido, Irvine, CA (US)

(73) Assignee: ALLERGAN SALES, LLC, North Chicago, IL (US)

( * ) Notice: Subject to any disclaimer, the term of this patent is extended or adjusted under 35 U.S.C. 154(b) by 362 days.

(21) Appl. No.: 17/112,911

(22) Filed: Dec. 4, 2020

(65) Prior Publication Data

US 2021/0254008 A1   Aug. 19, 2021

Related U.S. Application Data

(60) Provisional application No. 62/977,002, filed on Feb. 14, 2020.

(51) Int. Cl.
| | |
|---|---|
| *C12N 5/077* | (2010.01) |
| *A61K 8/64* | (2006.01) |
| *A61K 8/97* | (2017.01) |
| *A61K 8/99* | (2017.01) |
| *A61K 35/33* | (2015.01) |
| *A61Q 19/00* | (2006.01) |

(52) U.S. Cl.
CPC ............ *C12N 5/0656* (2013.01); *A61K 8/64* (2013.01); *A61K 8/97* (2013.01); *A61K 8/99* (2013.01); *A61K 35/33* (2013.01); *A61Q 19/00* (2013.01); *C12N 2500/02* (2013.01); *C12N 2500/32* (2013.01); *C12N 2513/00* (2013.01)

(58) Field of Classification Search
None
See application file for complete search history.

(56) References Cited

U.S. PATENT DOCUMENTS

| | | | |
|---|---|---|---|
| 5,830,708 A | 11/1998 | Naughton | |
| 5,833,948 A | 11/1998 | Tournier et al. | |
| 6,280,284 B1 | 8/2001 | Winefordner et al. | |
| 6,372,494 B1 | 4/2002 | Naughton et al. | |
| 7,118,746 B1 | 10/2006 | Naughton et al. | |
| 8,138,147 B2 | 3/2012 | Naughton et al. | |
| 8,158,879 B2 | 4/2012 | McGregor et al. | |
| 8,257,947 B2 * | 9/2012 | Naughton ............... A61P 29/00 435/395 | |
| 8,361,485 B2 | 1/2013 | Naughton et al. | |
| 8,476,231 B2 | 7/2013 | Naughton et al. | |
| 9,034,312 B2 | 5/2015 | Naughton et al. | |
| 9,119,974 B2 * | 9/2015 | Al-Qahtani ............ A61K 8/985 | |
| 9,168,214 B2 | 10/2015 | Brem et al. | |
| 9,408,881 B2 | 8/2016 | Gruber et al. | |
| 9,458,486 B2 | 10/2016 | Naughton et al. | |
| 2002/0019339 A1 | 2/2002 | Naughton | |
| 2002/0038152 A1 | 3/2002 | Naughton | |
| 2002/0122790 A1 | 9/2002 | Hunziker et al. | |
| 2004/0219134 A1 | 11/2004 | Naughton et al. | |
| 2009/0136459 A1 * | 5/2009 | Wu .......................... A61P 17/02 435/391 |
| 2012/0076842 A1 | 3/2012 | Fournial et al. | |
| 2012/0093885 A1 | 4/2012 | Sahoo et al. | |
| 2012/0225029 A1 * | 9/2012 | Al-Qahtani ............. A61P 17/00 424/85.4 |
| 2014/0127286 A1 * | 5/2014 | Doucet ................. A61K 8/9789 424/773 |
| 2017/0209365 A1 | 7/2017 | Cho et al. | |
| 2017/0216195 A1 | 8/2017 | Ames et al. | |
| 2018/0066307 A1 | 3/2018 | Ter-Ovanesyan et al. | |
| 2018/0147420 A1 | 5/2018 | Ludlow et al. | |
| 2018/0289767 A1 | 10/2018 | Garruto et al. | |
| 2019/0133922 A1 | 5/2019 | Kang et al. | |
| 2019/0314469 A1 | 10/2019 | Chang et al. | |
| 2020/0121722 A1 | 4/2020 | Yi et al. | |
| 2020/0215118 A1 | 7/2020 | Hong et al. | |
| 2020/0222298 A1 | 7/2020 | Yi et al. | |
| 2020/0276233 A1 | 9/2020 | Yi et al. | |
| 2020/0329697 A1 | 10/2020 | Kim et al. | |
| 2020/0338136 A1 | 10/2020 | Kim et al. | |
| 2021/0060081 A1 | 3/2021 | Kim et al. | |
| 2021/0161798 A1 | 6/2021 | Yi et al. | |
| 2021/0186831 A1 | 6/2021 | Cheng et al. | |
| 2021/0189329 A1 | 6/2021 | Levenberg et al. | |
| 2021/0196759 A1 | 7/2021 | Moseley et al. | |
| 2021/0290671 A1 | 9/2021 | Wehling et al. | |
| 2021/0393701 A1 | 12/2021 | O'Heeron et al. | |

FOREIGN PATENT DOCUMENTS

| | | | | |
|---|---|---|---|---|
| CN | 110592151 A | * | 12/2019 | ............... A61K 8/44 |
| WO | 2005054446 | | 6/2005 | |
| WO | WO-2011006107 A1 | * | 1/2011 | ............. A61K 38/00 |

OTHER PUBLICATIONS

Kosa, M., & Ragauskas, A. J. (2011). Lipids from heterotrophic microbes: advances in metabolism research. Trends in biotechnology, 29(2), 53-61. (Year: 2011).*
Putnins et al. Keratinocyte growth factor (KGF) promotes keratinocyte cell attachment and migration on collagen and fibronectin. Cell Adhesion and Communication 1999, 7;3:211-221. (Year: 1999).*
Belleudi et al. FGF7/KGF regulates autophagy in keratinocytes. Autophagy 2014, 10;5:803-821. (Year: 2014).*
Westergren-Thorsson et al. Transforming growth factor-ß induces selective increase of proteoglycan production and changes the copolymeric structure of dermatan sulphate in human skin fibroblasts. European Journal of Biochemistry 1992, 205:277-286. (Year: 1992).*
Feru et al. Aging decreases collage IV expression in vivo in the dermo-epidermal junction and in vitro in dermal fibroblasts: possible involvement of TGF-β. European Journal of Dermatology 2016, 26;4:350-360. (Year: 2016).*

(Continued)

*Primary Examiner* — Allison M Fox
*Assistant Examiner* — Jennifer S Spence
(74) *Attorney, Agent, or Firm* — Florek & Endres PPLC

(57) ABSTRACT

The production and use of extracellular matrix or conditioned medium compositions and more specifically to compositions obtained by culturing cells under hypoxic conditions on a surface in a suitable growth medium.

12 Claims, No Drawings

(56) References Cited

OTHER PUBLICATIONS

Agholme et al. Wnt signaling and orthopedics, an overview. Acta Orthopaedica 2011, 82;2:125-130. (Year: 2011).*

Carter et al. The role of integrins α2β1 and α3β1 in cell-cell and cell-substrate adhesion of human epidermal cells. Journal of Cell Biology 1990, 110:1387-1404. (Year: 1990).*

Choi et al. Restoration of senescent human diploid fibroblasts by modulation of the extracellular matrix. Aging Cell 2011, 10:148-157. (Year: 2011).*

CN 110592151 A, machine translation. (Year: 2019).*

López-Otin C, et al., "The Hallmarks of Aging," Cell. Jun. 6, 2013;153(6):1194-217.

Fabi et al., "The Potential of Topical and Injectable Growth Factors and Cytokines for Skin Rejuvenation," Facial Plastic Surgery. Apr. 2014;30(02):157-71.

Fitzpatrick et al., "Reversal of Photodamage with Topical Growth Factors: A Pilot Study," Journal of Cosmetic and Laser Therapy. Jan. 1, 2003;5(1):25-34.

Mehta et al. "Reduction in Facial Photodamage by a Topical Growth Factor Product," Journal of Drugs in Dermatology, Sep. 2008;7(9):864-871.

Kadoya et al., "Upregulation of Extracellular Matrix Genes Corroborates Clinical Efficacy of Human Fibroblast-Derived Growth Factors in Skin Rejuvenation," Journal of Drugs in Dermatology, Dec. 1, 2017;16(12):1190-6.

Mehta, "Growth Factors: The Science Behind Skin Rejuvenation," posted to the SKINMEDICA website on Jun. 12, 2016.

TNS Essential Serum® product information available on the SKINMEDICA website on Jan. 23, 2017.

TNS Essential Serum® product information available on the SKINMEDICA website on Feb. 13, 2019.

TNS® Advanced + Serum Healthcare Provider Presentation, Generational Dermatology conference Feb. 15, 2020, Palm Springs, California.

* cited by examiner

CONDITIONED MEDIUM FROM CELLS CULTURED UNDER HYPOXIC CONDITIONS AND USES THEREOF

FIELD

The present invention relates to the production and use of extracellular matrix or conditioned medium compositions and more specifically to compositions obtained by culturing cells under hypoxic conditions on a surface in a suitable growth medium. Use of the composition is also contemplated.

BACKGROUND OF THE INVENTION

Conditioned medium from in vitro studies and their use in a variety of therapeutic and medical applications have been described in the art. One therapeutic application of extracellular matrix (ECM) compositions includes the treatment and repair of soft tissue and skin defects such as wrinkles and scars.

The conditioned medium compositions may include amino acids, salts, vitamins, minerals sugars, lipids, nucleosides and proteins. The conditioned medium may contain many of the original components of the cell culture medium as well as a variety of cellular metabolites and secreted proteins including, for example, biologically active growth factors, inflammatory mediators and other extracellular proteins.

The repair or augmentation of soft tissue defects caused by acne, surgical scarring or aging has proven to be very difficult. A number of materials have been used to correct soft tissue defects with varying degrees of success, however, no material has been completely safe and effective. For example, silicon causes a variety of physiological and clinical problems including long term side effects such as nodules, recurring cellulitis and skin ulcers.

Accordingly, new materials are needed for soft tissue repair and treatment of soft tissue that may overcome the deficiencies of prior materials.

In vitro cultured medium can also be used to treat damaged soft tissue such as dermal tissue, for example.

In vitro cultured medium can additionally be used to repair and/or regenerate damaged cells or tissue such as dermal tissue, for example. The compositions of the present invention may be useful for treatment of trauma to the skin such as burns, laser treatment, and the effects of aging. Effects of aging may include skin discoloration, uneven skin texture, roughness and uneven skin tone, for example.

Fueled in part by the stem cell revolution, tissue engineering technology offers the promise of tissue regeneration and replacement following trauma or treatment of degenerative diseases. It can also be used in the context of cosmetic procedures.

Tissue engineering techniques can be used to generate both autologous and heterologous tissue or cells using a variety of cell types and culture techniques. In creating an autologous implant, donor tissue may be harvested and dissociated into individual cells, and subsequently attached and cultured on a substrate to be implanted at the desired site of the functioning tissue. Many isolated cell types can be expanded in vitro using cell culture techniques, however, anchorage dependent cells require specific environments, often including the presence of a three-dimensional scaffold, to act as a template for growth.

Thus, the development of natural materials that are suitable for topical application is greatly needed.

SUMMARY

The embodiments herein encompass methods and compositions comprising human fibroblast-derived cell culture medium that is cultured under hypoxic conditions.

In a first aspect, a method of producing a composition for improvement of tissue in a subject is provided, the method comprising: culturing human fibroblast cells under hypoxic conditions on microcarrier beads or a three dimensional surface in a suitable cell culture medium under 1-5% oxygen, thereby simulating the early embryonic environment, and generating a composition with embryonic-like proteins that promotes the repair and regeneration of damaged tissue when administered to the region of tissue in need of repair. In some embodiments, the method further comprises adding at least one botanical to the composition. In some embodiments, the method further comprises adding at least one extract to the composition. In some embodiments, the method further comprises adding at least one peptide to the composition. In some embodiments, the culturing is performed on microcarrier beads or a three-dimensional surface in a suitable cell culture medium. In some embodiments, the culturing is performed for at least two weeks. In some embodiments, the conditioned medium is collected after two weeks. In some embodiments, the method further comprises adding a seed extract to the composition. In some embodiments, the method further comprises adding a marine extract to the composition. In some embodiments, the method further comprises adding a bacterial ferment to the composition. In some embodiments, the conditioned medium has embryonic-like proteins. In some embodiments, the conditioned medium further comprises cytokines. In some embodiments, the conditioned medium further comprises at least one matrix protein. In some embodiments, the at least one peptide comprises dimer tripeptide 43 and/or trifluoroacetyl tripeptide-2. In some embodiments, the subject is in need of tissue repair. In some embodiments, the subject has fine and or deep wrinkles. In some embodiments, the subject exhibits tactile and/or skin roughness of the tissue. In some embodiments, the subject has hyperpigmentation. In some embodiments, the subject has photodamage. In some embodiments, the subject lacks evenness in pigmentation and/or skin tone. In some embodiments, the subject has a skin coloring on the Fitzpatrick scale of 1, 2, 3, 4 or 5.

In a second aspect, a composition made by the method of any one of the embodiments described herein is provided for use in treating a subject.

In a third aspect, a composition is prepared from a conditioned medium that is prepared from a cell culture medium cultured with embryonic-like proteins under hypoxic conditions, at least one botanical, at least one extract and at least one peptide. In some embodiments, the composition is odorless. In some embodiments, the composition is clear.

In a fourth aspect, a method of improving the appearance of an individual is provided, the method comprising: topically applying a composition of any one of the embodiments described herein onto the surface of a subject's skin to thereby improve the aesthetic quality of the skin. In some embodiments, the subject has fine or deep wrinkles. In some embodiments, the subject has tactile and/or skin roughness of the tissue. In some embodiments, the subject has loose or sagging skin. In some embodiments, the method improves roughness of skin. In some embodiments, the method restores volume moisture to the tissue. In some embodiments, the method results in reduced inflammatory response of the tissue. In some embodiments, the subject is in need of tissue repair. In some embodiments, the subject is suffering from a burn wound. In some embodiments, the method leads to healing of the tissue. In some embodiments, the skin is protected from free radical damage. In some embodiments, the composition supports epidermal cell-cell adhesion. In some embodiments, the composition supports a dermal epidermal junction. In some embodiments, the composition supports stem cells function and proliferation. In some embodiments, the composition supports intercellular communication. In some embodiments, the composition supports cellular recycling and protein homeostasis. In some embodiments, the composition prevents cellular senescence. In some embodiments, the composition supports collagen, elastin and other ECM components. In some embodiments, the composition supports heparan sulfate and proteoglycans.

DETAILED DESCRIPTION

The section headings used herein are for organizational purposes only and are not to be construed as limiting the subject matter described.

Where the definition of terms as used in the specification departs from the commonly used meaning of the term, applicant intends to utilize the definitions provided herein, unless specifically indicated.

Treating soft tissue defects that may arise from aging has proven to be quite challenging. A number of materials have been used to correct soft tissue defects with varying degrees of success, however, no material has been found to be completely safe and effective. For example, silicon causes a variety of physiological and clinical problems including long term side effects, such as nodules, recurring cellulitis and skin ulcers.

Aging leads to defects including but not limited to fine lines and deep wrinkles, hyperpigmentation, elastin degradation, collagen degradation, inflammation, and decreased fibroblast function.

In some embodiments, a method for making compositions that include one or more proteins that are expressed during hypoxic conditions is provided. These proteins may be embryonic proteins, for example. In particular, the compositions are generated by culturing cells under hypoxic conditions on a surface (e.g., two-dimensional or three-dimensional) in a suitable growth medium. The culturing method produces both soluble and non-soluble fractions which may be used separately or in combination to obtain physiologically acceptable compositions having a variety of applications. The hypoxic conditions may induce proteins that stimulate precursor cells and may further strengthen the skin rejuvenating benefits of human fibroblast-derived growth factors.

In certain embodiments, a composition for repair and regeneration of skin tissue on a subject is disclosed comprising a conditioned medium collected from culturing human fibroblast cells under hypoxic conditions in a suitable cell culture medium and at least one additive, wherein the conditioned medium is stored in a first container and the additive is stored in a second container, and wherein the conditioned medium and the additive are mixed prior to application to the skin tissue. The first container and the second container are separate chambers in a dual chamber container.

In certain embodiments, the human fibroblast cells are cultured under hypoxic conditions on a substrate grown in a suitable cell culture medium under 1-5% oxygen thereby producing embryo-like properties. The substrate may be microcarrier beads or a three-dimensional surface.

The compositions of the present invention may be colorless and further comprise at least one botanical or botanical extract in a range of about 0.5 to about 2.0% by weight of the composition, at least one peptide present within a range of about 0.0001 to about 0.001% by weight of the composition, at least one seed extract present within a range of about 0.5 to about 2% by weight of the composition, at least one marine extract within a range of about 0.01 to about 0.1% by weight of the composition, at least one bacterial ferment present within a range of about 0.5 to about 3.0% by weight of the composition, stem cell factors present within a range of about 0.1 to about 30% by weight of the composition, and/or cytokines.

In some embodiments, the composition may include cellular cytokines and growth factors. Extracellular proteins may be secreted into conditioned cell media such as growth factors, cytokines, and stress proteins. These may be used in the preparation of products for use in a large variety of areas including tissue repair, e.g., in the treatment of wounds and other tissue defects such as cosmetic defects as well as human and animal feed supplements. For example, growth factors are known to play an important role in the wound healing process. In general, it is thought desirable in the treatment of wounds to enhance the supply of growth factors by direct addition of these factors.

Cellular cytokines and growth factors are involved in a number of critical cellular processes including cell proliferation, adhesion, morphologic appearance, differentiation, migration, inflammatory responses, angiogenesis, and cell death. Studies have demonstrated that hypoxic stress and injury to cells induce responses including increased levels of mRNA and proteins corresponding to growth factors such as PDGF (platelet-derived growth factor), VEGF (vascular endothelial growth factor), FGF (fibroblast growth factor), and IGF (insulin-like growth factor) (Gonzalez-Rubio, M. et al., 1996, *Kidney Int.* 50(1):164-73; Abramovitch, R. et al., 1997, *Int J. Exp. Pathol.* 78(2):57-70; Stein, I. et al., 1995, *Mol Cell Biol.* 15(10):5363-8; Yang, W. et al., 1997, FEBS Lett. 403(2):139-42; West, N. R. et al., 1995, *J Neurosci. Res.* 40(5):647-59).

The growth factors are naturally secreted proteins which may regulate a variety of cell functions.

In some embodiments, the composition includes proteins that stimulate precursor cells.

The compositions of the present invention have a variety of applications including, but not limited to, promoting repair and/or regeneration of damaged cells or tissues, use in patches and implants to promote tissue regeneration (e.g., hernial repair, pelvic floor repair, rotator cuff repair, and wound repair), use in tissue culture systems for culturing cells, such as stem cells, use in surface coatings used in association with implantable devices (e.g., pacemakers, stents, stent grafts, vascular prostheses, heart valves, shunts, drug delivery ports or catheters, hernial and pelvic floor repair patches), promoting soft tissue repair, augmentation, and/or improvement of a skin surface, such as wrinkles, use as a biological anti-adhesion agent or as a biological vehicle for cell delivery or maintenance at a site of delivery.

In some embodiments, compositions comprising the cultured medium may be used for the treatment of wrinkles (deep wrinkles, fine lines), wound healing, scar healing, hyperpigmentation, uneven skin tone, dry skin, tactile and/or skin roughness, and/or treatment of scarring.

The embodiments described herein are based in part, on the discovery that cells cultured on three-dimensional surfaces under conditions that stimulate the early embryonic environment (hypoxia and reduced gravitational forces) prior to angiogenesis produces ECM compositions with fetal properties, including generation of embryonic proteins. Growth of cells under hypoxic conditions demonstrate a unique ECM with fetal properties and growth factor expression. Unlike the culturing of ECM under traditional culture conditions, over 5000 genes are differentially expressed in ECM cultured under hypoxic conditions. This results in a cultured ECM that has different properties and a different biological composition. For example, an ECM produced under hypoxic conditions is similar to fetal mesenchymal tissue in that it is relatively rich in collagens type III, IV, and V, and glycoproteins such as fibronectin, SPARC, thrombospondin, and hyaluronic acid.

In some embodiments, the hypoxic conditions induce proteins that stimulate precursor cells.

Hypoxia also enhances expression of factors which regulate wound healing and organogenesis, such as VEGF, FGF-7, and TGF-β, as well as multiple Wnt factors including writs 2b, 4, 7a, 10a, and 11. Cultured embryonic human ECM also stimulates an increase of metabolic activity in human fibroblasts in vitro, as measured by increased enzymatic activity. Additionally, there is an increase in cell number in response to the cultured embryonic ECM.

Before the present compositions and methods are described, it is to be understood that embodiments described herein are not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

In some embodiments, methods for making compositions comprising one or more embryonic-like proteins and applications thereof are provided. In particular, the compositions are generated by culturing cells under hypoxic conditions on a two-dimensional or three-dimensional surface in a suitable cell culture medium. The compositions are derived by growing cells on a three-dimensional framework resulting in a multi-layer cell culture system. Cells grown on a three-dimensional framework support, in accordance with the present invention, grow in multiple layers, forming a cellular matrix. Growth of the cultured cells under hypoxic conditions results in differential gene expression as the result of hypoxic culturing conditions versus traditional culture.

An ECM is a composition of proteins and biopolymers that substantially comprise tissue that is produced by cultivation of cells. Stromal cells, such as fibroblasts, are an anchorage dependent cell type requiring growth while attached to materials and surfaces suitable for cell culture. The ECM produced by the cultured cells are deposited in a three-dimensional arrangement providing spaces for the formation of tissue-like structures.

The cultivation materials providing three-dimensional architectures are referred to as scaffolds. Spaces for deposition of the ECM are in the form of openings within, for example woven mesh or interstitial spaces created in a compacted configuration of spherical beads, called microcarriers.

As used herein, "ECM" or "extracellular matrix composition" includes soluble and non-soluble fractions or any portion thereof. The non-soluble fraction of an ECM includes those secreted proteins and biological components that are deposited on the support or scaffold. The soluble fraction includes refers to culture media in which cells have been cultured and into which the cells have secreted active agent(s) and includes those proteins and biological components not deposited on the scaffold. Both fractions may be collected, and optionally further processed, and used individually or in combination in a variety of applications as described herein.

The three-dimensional support or scaffold used to culture stromal cells may be of any material and/or shape that: (a) allows cells to attach to it (or can be modified to allow cells to attach to it); and (b) allows cells to grow in more than one layer (i.e., form a three dimensional tissue). In some embodiments, a substantially two-dimensional sheet or membrane or beads may be used to culture cells that are sufficiently three dimensional in form.

The biocompatible material is formed into a three-dimensional structure or scaffold, where the structure has interstitial spaces for attachment and growth of cells into a three-dimensional tissue. The openings and/or interstitial spaces of the framework in some embodiments are of an appropriate size to allow the cells to stretch across the openings or spaces. Maintaining actively growing cells stretched across the framework appears to enhance production of the repertoire of growth factors responsible for the activities described herein. If the openings are too small, the cells may rapidly achieve confluence but be unable to easily exit from the mesh. These trapped cells may exhibit contact inhibition and cease production of the appropriate factors necessary to support proliferation and maintain long term cultures. If the openings are too large, the cells may be unable to stretch across the opening, which may lead to a decrease in stromal cell production of the appropriate factors necessary to support proliferation and maintain long term cultures. Typically, the interstitial spaces are at least about 100 um, at least about 140 um, at least about 150 um, at least about 180 um, at least about 200 um, or at least about 220 um. When using a mesh type of matrix, as exemplified herein, the openings range from about 100 μm to about 220 μm. However, depending upon the three-dimensional structure and intricacy of the framework, other sizes are permissible. Any shape or structure that allows the cells to stretch and continue to replicate and grow for lengthy time periods may function to elaborate the cellular factors in accordance with the methods herein.

In some aspects, the three dimensional framework is formed from polymers or threads that are braided, woven, knitted or otherwise arranged to form a framework, such as a mesh or fabric. The materials may also be formed by casting of the material or fabrication into a foam, matrix, or sponge-like scaffold. In other aspects, the three-dimensional framework is in the form of matted fibers made by pressing polymers or other fibers together to generate a material with interstitial spaces. The three-dimensional framework may take any form or geometry for the growth of cells in culture. Thus, other forms of the framework, as further described below, may suffice for generating the appropriate conditioned medium.

A number of different materials may be used to form the scaffold or framework. These materials include non-polymeric and polymeric materials. Polymers, when used, may be any type of polymer, such as homopolymers, random polymers, copolymers, block polymers, coblock polymers (e.g., di, tri, etc.), linear or branched polymers, and crosslinked or non-crosslinked polymers. Non-limiting examples of materials for use as scaffolds or frameworks include, among others, glass fibers, polyethylenes, polypropylenes, polyamides (e.g., nylon), polyesters (e.g., dacron), polystyrenes, polyacrylates, polyvinyl compounds (e.g., polyvinylchloride; PVC), polycarbonates, polytetrafluorethylenes (PTFE; TEFLON), thermanox (TPX), nitrocellulose, polysaacharides (e.g., celluloses, chitosan, agarose), polypeptides (e.g., silk, gelatin, collagen), polyglycolic acid (PGA), and dextran.

In some embodiments, the framework or beads may be made of materials that degrade over time under the conditions of use. Biodegradable also refers to absorbability or degradation of a compound or composition when administered in vivo or under in vitro conditions. Biodegradation may occur through the action of biological agents, either directly or indirectly. Non-limiting examples of biodegradable materials include, among others, polylactide, polyglycolide, poly(trimethylene carbonate), poly(lactide-co-glycolide) (i.e., PLGA), polyethylene terephtalate (PET), polycaprolactone, catgut suture material, collagen (e.g., equine collagen foam), polylactic acid, or hyaluronic acid. For example, these materials may be woven into a three-dimensional framework such as a collagen sponge or collagen gel.

In other aspects, where the cultures are to be maintained for long periods of time, cryopreserved, and/or where additional structural integrity is desired, the three dimensional framework may be comprised of a nonbiodegradable material. As used herein, a nonbiodegradable material refers to a material that does not degrade or decompose significantly under the conditions in the culture medium. Exemplary nondegradable materials include, as non-limiting examples, nylon, dacron, polystyrene, polyacrylates, polyvinyls, polytetrafluoroethylenes (PTFE), expanded PTFE (ePTFE), and cellulose. An exemplary nondegrading three dimensional framework comprises a nylon mesh, available under the tradename Nitex®, a nylon filtration mesh having an average pore size of 140 µm and an average nylon fiber diameter of 90 µm (#3-210/36, Tetko, Inc., N.Y.).

In other aspects, the beads, scaffold or framework is a combination of biodegradeable and non-biodegradeable materials. The non-biodegradable material provides stability to the three dimensional scaffold during culturing while the biodegradeable material allows formation of interstitial spaces sufficient for generating cell networks that produce the cellular factors sufficient for therapeutic applications. The biodegradable material may be coated onto the non-biodegradable material or woven, braided or formed into a mesh. Various combinations of biodegradable and non-biodegradable materials may be used. An exemplary combination is poly(ethylene therephtalate) (PET) fabrics coated with a thin biodegradable polymer film, poly[D-L-lactic-co-glycolic acid), in order to obtain a polar structure.

In various aspects, the scaffold or framework material may be pre-treated prior to inoculation with cells to enhance cell attachment. For example, prior to inoculation with cells, nylon screens in some embodiments are treated with 0.1 M acetic acid, and incubated in polylysine, fetal bovine serum, and/or collagen to coat the nylon. Polystyrene could be similarly treated using sulfuric acid. In some embodiments, the growth of cells in the presence of the three-dimensional support framework may be further enhanced by adding to the framework or coating it with proteins (e.g., collagens, elastin fibers, reticular fibers), glycoproteins, glycosaminoglycans (e.g., heparan sulfate, chondroitin-4-sulfate, chondroitin-6-sulfate, dermatan sulfate, keratan sulfate, etc.), fibronectins, and/or glycopolymer (poly[N-p-vinylbenzyl-D-lactoamide], PVLA) in order to improve cell attachment. Treatment of the scaffold or framework is useful where the material is a poor substrate for the attachment of cells.

In one aspect, mesh is used for production of ECM. The mesh is a woven nylon 6 material in a plain weave form with approximately 100 µm openings and approximately 125 µm thick. In culture, fibroblast cells attach to the nylon through charged protein interactions and grow into the voids of the mesh while producing and depositing ECM proteins. Mesh openings that are excessively large or small may not be effective but could differ from those above without substantially altering the ability to produce or deposit ECM. In another aspect, other woven materials are used for ECM production, such as polyolefin's, in weave configurations giving adequate geometry for cell growth and ECM deposition.

For example, nylon mesh is prepared for cultivation in any of the steps of the invention by cutting to the desired size, washing with 0.1-0.5M acetic acid followed by rinsing with high purity water and then steam sterilized. For use as a three-dimensional scaffold for ECM production the mesh is sized into squares approximately 10 cm×10 cm. However, the mesh could be any size appropriate to the intended application and may be used in any of the methods of the present invention, including cultivation methods for inoculation, cell growth and ECM production and preparation of the final form.

In other aspects, the scaffold for generating the cultured tissues is composed of microcarriers, which are beads or particles. The beads may be microscopic or macroscopic and may further be dimensioned so as to permit penetration into tissues or compacted to form a particular geometry. In some embodiments of any one of each or any of the above- or below-mentioned embodiments of the tissue penetrating embodiments, the framework for the cell cultures comprises particles that, in combination with the cells, form a three dimensional tissue. The cells attach to the particles and to each other to form a three dimensional tissue. The complex of the particles and cells is of sufficient size to be administered into tissues or organs, such as by injection or catheter. Beads or microcarriers are typically considered a two-dimensional system or scaffold.

As used herein, a "microcarrier" refers to a particle having a size in the range of of nanometers to micrometers in any shape or geometry, including but not limited to being irregular, non-spherical, spherical, or ellipsoid.

The size of the microcarriers suitable for the purposes herein can be of any size suitable for the particular application. In some embodiments, the size of microcarriers suitable for the three dimensional tissues may be those administrable by injection. In some embodiments, the microcarriers have a particle size range of at least about 1 µm, at least about 10 µm, at least about 25 µm, at least about 50 µm, at least about 100 µm, at least about 200 µm, at least about 300 µm, at least about 400 µm, at least about 500 µm, at least about 600 µm, at least about 700 µm, at least about 800 µm, at least about 900 µm, at least about 1000 µm.

In some embodiments, the microcarriers are made of biodegradable materials. In some embodiments, microcarriers comprising two or more layers of different biodegradable polymers may be used. In some embodiments, at least an outer first layer has biodegradable properties for forming the three dimensional tissues in culture, while at least a biodegradable inner second layer, with properties different from the first layer, is made to erode when administered into a tissue or organ.

In some embodiments, the microcarriers are porous microcarriers. Porous microcarriers refer to microcarriers having interstices through which molecules may diffuse in or out from the microparticle. In some embodiments, the microcarriers are non-porous microcarriers. A nonporous microparticle refers to a microparticle in which molecules of a select size do not diffuse in or out of the microparticle.

Microcarriers for use in the compositions are biocompatible and have low or no toxicity to cells. Suitable microcarriers may be chosen depending on the tissue to be treated, type of damage to be treated, the length of treatment desired, longevity of the cell culture in vivo, and time required to form the three dimensional tissues. The microcarriers may comprise various polymers, natural or synthetic, charged (i.e., anionic or cationic) or uncharged, biodegradable, or nonbiodegradable. The polymers may be homopolymers, random copolymers, block copolymers, graft copolymers, and branched polymers.

In some embodiments, the microcarriers comprise non-biodegradable microcarriers. Non-biodegradable microcapsules and microcarriers include, but not limited to, those made of polysulfones, poly(acrylonitrile-co-vinyl chloride), ethylene-vinyl acetate, hydroxyethylmethacrylate-methylmethacrylate copolymers. These are useful to provide tissue bulking properties or in embodiments where the microcarriers are eliminated by the body.

In some embodiments, the microcarriers comprise degradable scaffolds. These include microcarriers made from naturally occurring polymers, non-limiting example of which include, among others, fibrin, casein, serum albumin, collagen, gelatin, lecithin, chitosan, alginate or poly-amino acids such as poly-lysine. In other aspects, the degradable microcarriers are made of synthetic polymers, non-limiting examples of which include, among others, polylactide (PLA), polyglycolide (PGA), poly(lactide-co-glycolide) (PLGA), poly(caprolactone), polydioxanone trimethylene carbonate, polyhybroxyalkonates (e.g., poly(hydroxybutyrate), poly(ethyl glutamate), poly(DTH iminocarbony(bisphenol A iminocarbonate), poly(ortho ester), and polycyanoacrylates.

In some embodiments, the microcarriers comprise hydrogels, which are typically hydrophilic polymer networks filled with water. Hydrogels have the advantage of selective trigger of polymer swelling. Depending on the composition of the polymer network, swelling of the microparticle may be triggered by a variety of stimuli, including pH, ionic strength, thermal, electrical, ultrasound, and enzyme activities. Non-limiting examples of polymers useful in hydrogel compositions include, among others, those formed from polymers of poly(lactide-co-glycolide); poly(N-isopropylacrylamide); poly(methacrylic acid-g-polyethylene glycol); polyacrylic acid and poly(oxypropylene-co-oxyethylene) glycol; and natural compounds such as chrondroitan sulfate, chitosan, gelatin, fibrinogen, or mixtures of synthetic and natural polymers, for example chitosan-poly(ethylene oxide). The polymers may be crosslinked reversibly or irreversibly to form gels adaptable for forming three dimensional tissues.

In some embodiments, the microcarriers or beads for use in the present invention are composed wholly or composed partly of dextran.

In accordance with the embodiments described herein, the culturing method is applicable to proliferation of different types of cells, including stromal cells such as fibroblasts, and particularly primary human neonatal foreskin fibroblasts. In some embodiments, the cells inoculated onto the scaffold or framework can be stromal cells comprising fibroblasts, with or without other cells, as further described below. In some embodiments, the cells are stromal cells that are typically derived from connective tissue, including, but not limited to: (1) bone; (2) loose connective tissue, including collagen and elastin; (3) the fibrous connective tissue that forms ligaments and tendons, (4) cartilage; (5) the ECM of blood; (6) adipose tissue, which comprises adipocytes; and (7) fibroblasts.

Stromal cells can be derived from various tissues or organs, such as skin, heart, blood vessels, bone marrow, skeletal muscle, liver, pancreas, brain, foreskin, which can be obtained by biopsy (where appropriate) or upon autopsy. In some embodiments, fetal fibroblasts can be obtained in high quantity from foreskin, such as neonatal foreskins.

In some embodiments, the cells comprise fibroblasts, which can be from a fetal, neonatal, adult origin, or a combination thereof. In some embodiments, the stromal cells comprise fetal fibroblasts, which can support the growth of a variety of different cells and/or tissues. As used herein, a fetal fibroblast refers to fibroblasts derived from fetal sources. As used herein, neonatal fibroblast refers to fibroblasts derived from newborn sources. Under appropriate conditions, fibroblasts can give rise to other cells, such as bone cells, fat cells, and smooth muscle cells and other cells of mesodermal origin. In some embodiments, the fibroblasts comprise dermal fibroblasts, which are fibroblasts derived from skin. Normal human dermal fibroblasts can be isolated from neonatal foreskin. These cells are typically cryopreserved at the end of the primary culture.

In some embodiments, the three-dimensional tissue can be made using stem or progenitor cells, either alone, or in combination with any of the cell types discussed herein. Stem and progenitor cells include, by way of example and not limitation, embryonic stem cells, hematopoietic stem cells, neuronal stem cells, epidermal stem cells, and mesenchymal stem cells.

In some embodiments, a "specific" three-dimensional tissue can be prepared by inoculating the three-dimensional scaffold with cells derived from a particular organ, i.e., skin, heart, and/or from a particular individual who is later to receive the cells and/or tissues grown in culture in accordance with the methods described herein.

For certain uses in vivo it is preferable to obtain the stromal cells from the patient's own tissues. The growth of cells in the presence of the three-dimensional stromal support framework can be further enhanced by adding to the framework, or coating the framework support with proteins, e.g., collagens, laminins, elastic fibers, reticular fibers, glycoproteins; glycosaminoglycans, e.g., heparin sulfate, chondroitin-4-sulfate, chondroitin-6-sulfate, dermatan sulfate, keratan sulfate, etc.; a cellular matrix, and/or other materials.

Thus, since the two-dimensional or three-dimensional culture systems described herein are suitable for growth of diverse cell types and tissues, and depending upon the tissue to be cultured and the collagen types desired, the appropriate stromal cells may be selected to inoculate the framework.

While the methods and applications of the present invention are suitable for use with different cell types, such as tissue specific cells or different types of stromal cells as discussed herein, derivation of the cells for use with the present invention may also be species specific. Accordingly, ECM compositions may be generated that are species specific. For example, the cells for use in the present invention may include human cells. For example, the cells may be human fibroblasts. Likewise, the cells are from another species of animal, such as equine (horse), canine (dog) or feline (cat) cells. Additionally, cells from one species or strain of species may be used to generate ECM compositions for use in other species or related strains (e.g., allogeneic, syngeneic and xenogeneic). It is also to be appreciated that cells derived from various species may be combined to generate multi-species ECM compositions.

Accordingly, the methods and compositions of the present invention are suitable in applications involving non-human animals. As used herein, "veterinary" refers to the medical science concerned or connected with the medical or surgical treatment of animals, especially domestic animals. Common veterinary animals may include mammals, amphibians, avians, reptiles and fishes. For example, typical mammals may include dogs, cats, horses, rabbits, primates, rodents, and farm animals, such as cows, horses, goats, sheep, and pigs.

As discussed above, additional cells may be present in the culture with the stromal cells. These additional cells may have a number of beneficial effects, including, among others, supporting long term growth in culture, enhancing synthesis of growth factors, and promoting attachment of cells to the scaffold. Additional cell types include as non-limiting examples, smooth muscle cells, cardiac muscle cells, endothelial cells, skeletal muscle cells, endothelial cells, pericytes, macrophages, monocytes, and adipocytes. Such cells may be inoculated onto the framework along with fibroblasts, or in some aspects, in the absence of fibroblasts. These stromal cells may be derived from appropriate tissues or organs, including, by way of example and not limitation, skin, heart, blood vessels, bone marrow, skeletal muscle, liver, pancreas, and brain. In other aspects, one or more other cell types, excluding fibroblasts, are inoculated onto the scaffold. In still other aspects, the scaffolds are inoculated only with fibroblast cells.

Fibroblasts may be readily isolated by disaggregating an appropriate organ or tissue which is to serve as the source of the fibroblasts. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, hyaluronidase, DNase, pronase, and/or dispase etc. Mechanical disruption can also be accomplished by a number of methods including, but not limited to the use of grinders, blenders, sieves, homogenizers, pressure cells, or insonators to name but a few. In some embodiments, excised foreskin tissue is treated using digestive enzymes, typically collagenase and/or trypsinase to disassociate the cells from encapsulating structures.

The isolation of fibroblasts, for example, can be carried out as follows: fresh tissue samples are thoroughly washed and minced in Hanks' balanced salt solution (HBSS) in order to remove serum. The minced tissue is incubated from 1-12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated fibroblasts can then be grown to confluency, lifted from the confluent culture and inoculated onto the three-dimensional framework, see Naughton et al., 1987, J. Med. 18(3&4):219-250. Inoculation of the three-dimensional framework with a high concentration of stromal cells, e.g., approximately $10^6$ to $5 \times 10^7$ cells/ml, will result in the establishment of the three-dimensional stromal support in shorter periods of time.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis and fluorescence-activated cell sorting. For a review of clonal selection and cell separation techniques, see Freshney, Culture of Animal Cells. A Manual of Basic Techniques, 2d Ed., A. R. Liss, Inc., New York, 1987, Ch. 11 and 12, pp. 137-168.

In some embodiments, isolated fibroblast cells can be grown to produce cell banks. Cell banks are created to allow for initiating various quantities and timing of cultivation batches and to allow preemptive testing of cells for contaminants and specific cellular characteristics. Fibroblasts from the cell banks are subsequently grown to increase cell number to appropriate levels for seeding scaffolds. Operations involving environmental exposure of cells and cell contacting materials are performed by aseptic practices to reduce the potential for contamination of foreign materials or undesirable microbes.

In some embodiments, after isolation, cells may be grown through several passages to a quantity suitable for building master cell banks. The cell banks can then be, harvested and filled into appropriate vessels and preserved in cryogenic conditions. Cells in frozen vials from master cell banks can be thawed and grown through additional passages (usually two or more). The cells can then be used to prepare cryogenically preserved working cell banks.

A cell expansion step uses vials of cells at the working cell bank stage to further increase cell numbers for inoculating three-dimensional scaffolds or supports, such as mesh or microcarriers. Each passage is a series of sub-culture steps that include inoculating cell growth surfaces, incubation, feeding the cells and harvesting.

Cultivation for cell banks and cell expansion can be conducted by inoculating culture vessels, such as culture flasks, roller bottles or microcarriers. Stromal cells, such as fibroblasts, attach to the intended growth surfaces and grow in the presence of culture media. Culture vessels, such as culture flasks, roller bottles and microcarriers are specifically configured for cell culture and are commonly made from various plastic materials qualified for intended applications. Microcarriers typically are microscopic or macroscopic beads and are typically made of various plastic materials. However, they can be made from other materials such as glasses or solid/semi-solid biologically based materials such as collagens or other materials such as Dextran, a modified sugar complex as discussed above.

During cultivation, expended media is periodically replaced with fresh media during the course of cell growth to maintain adequate availability of nutrients and removal of inhibitory products of cultivation. Culture flasks and roller bottles provide a surface for the cells to grow onto and are typically used for cultivation of anchorage dependent cells.

In some embodiments, incubation is performed in a chamber heated at 37° C. Cultivation topologies requiring communication of media and the chamber environment use a 5% $CO_2$ v/v with air in the chamber gas space to aid in regulation of pH. Alternately, vessels equipped to maintain cultivation temperature and pH can be used for both cell expansion and ECM production operations. Temperatures below 35° C. or above 38° C. and $CO_2$ concentrations below 3% or above 12% may not be appropriate.

Harvesting cells from attachment surfaces can conducted by removal of growth media and rinsing the cells with a buffered salt solution to reduce enzyme competing protein, application of disassociating enzymes then neutralization of the enzymes after cell detachment. Harvested cell suspension is collected and harvest fluids are separated by centrifugation. Cell suspensions from sub-culture harvests can be sampled to assess the quantity of cells recovered and other cellular attributes and are subsequently combined with fresh media and applied as inoculums. The number of passages used for preparing cell banks and scaffold inoculum is critical with regard to achieving acceptable ECM characteristics.

After an appropriate three-dimensional scaffold is prepared, it is inoculated by seeding with the prepared stromal cells. Inoculation of the scaffold may be done in a variety of ways, such as sedimentation. Mesh prepared for culture of ECM under aerobic conditions are prepared in the same manner as for hypoxic grown mesh with the exception that an anaerobic chamber is not used to create hypoxic conditions.

For example, for both mesh prepared for culture of ECM under both aerobic and hypoxic conditions, prepared and sterilized mesh is placed in sterile 150 mm diameter×15 mm deep petri dishes and stacked to a thickness of approximately 10 pieces. Stacks of mesh are then inoculated by sedimentation. Cells are added to fresh media to obtain the appropriate concentration of cells for inoculum. Inoculum is added to the stack of mesh where cells settle onto the nylon fibers and attach while in incubated conditions. After an adequate time, individually seeded mesh sheets can be aseptically separated from the stack and placed individually into separate 150 mm×15 mm petri dishes containing approximately 50 ml of growth media.

In some embodiments, incubation of the inoculated culture is performed under hypoxic conditions. Incubation under hypoxic conditions may produce an ECM and surrounding media with unique properties as compared to ECM generated under normal culture conditions. As used herein, hypoxic conditions are characterized by a lower oxygen concentration as compared to the oxygen concentration of ambient air (approximately 15%-20% oxygen). In one aspect, hypoxic conditions are characterized by an oxygen concentration less than about 10%. In another aspect, hypoxic conditions are characterized by an oxygen concentration of about 1% to 10%, 1% to 9%, 1% to 8%, 1% to 7%, 1% to 6%, 1% to 5%, 1% to 4%, 1% to 3%, or 1% to 2%. In a certain aspect, the system maintains about 1-3% oxygen within the culture vessel. Hypoxic conditions can be created and maintained by using a culture apparatus that allows one to control ambient gas concentrations, for example, an anaerobic chamber.

Incubation of cell cultures is typically performed in normal atmosphere with 15-20% oxygen and 5% $CO_2$ for expansion and seeding, at which point low oxygen cultures are split to an airtight chamber that is flooded with 95% nitrogen/5% $CO_2$ so that a hypoxic environment is created within the culture medium.

For example, petri dishes with mesh cultured for producing ECM under hypoxic conditions are initially grown in incubation at 37° C. and 95% air/5% $CO_2$ for 2-3 weeks. Following the period of near atmospheric cultivation, the petri dishes of mesh are incubated in a chamber designed for anaerobic cultivation that is purged with a gas mixture of approximately 95% nitrogen and 5% $CO_2$. Expended growth media is replaced with fresh media at atmospheric oxygen level through the culture period and after media is exchanged the mesh filled petri dishes are place in the anaerobic chamber, the chamber is purged with 95% nitrogen/5% $CO_2$ then incubated at 37° C. Cultured mesh are harvested when they reach the desired size or contain the desire biological components.

During the incubation period, the stromal cells will grow linearly along and envelop the three-dimensional framework before beginning to grow into the openings of the framework. The growing cells produce a myriad of growth factors, regulatory factors and proteins, some of which are secreted in the surrounding media, and others that are deposited on the support to make up the ECM more fully discussed below. Growth and regulatory factors can be added to the culture, but are not necessary. Culture of the stromal cells produces both non-soluble and soluble fractions. The cells are grown to an appropriate degree to allow for adequate deposition of ECM proteins.

During culturing of the three-dimensional tissues, proliferating cells may be released from the framework and stick to the walls of the culture vessel where they may continue to proliferate and form a confluent monolayer. To minimize this occurrence, which may affect the growth of cells, released cells may be removed during feeding or by transferring the three-dimensional cell culture to a new culture vessel. Removal of the confluent monolayer or transfer of the cultured tissue to fresh media in a new vessel maintains or restores proliferative activity of the three-dimensional cultures. In some aspects, removal or transfers may be done in a culture vessel which has a monolayer of cultured cells exceeding 25% confluency. Alternatively, the culture in some embodiments is agitated to prevent the released cells from sticking; in others, fresh media is infused continuously through the system. In some aspects, two or more cell types can be cultured together either at the same time or one first followed by the second (e.g., fibroblasts and smooth muscle cells or endothelial cells).

After inoculation of the three dimensional scaffolds, the cell culture is incubated in an appropriate nutrient medium and incubation conditions that supports growth of cells into the three dimensional tissues. Many commercially available media such as Dulbecco's Modified Eagles Medium (DMEM), RPMI 1640, Fisher's, Iscove's, and McCoy's, may be suitable for supporting the growth of the cell cultures. The medium may be supplemented with additional salts, carbon sources, amino acids, serum and serum components, vitamins, minerals, reducing agents, buffering agents, lipids, nucleosides, antibiotics, attachment factors, and growth factors. Formulations for different types of culture media are described in various reference works available to the skilled artisan (e.g., Methods for Preparation of Media, Supplements and Substrates for Serum Free Animal Cell Cultures, Alan R. Liss, New York (1984); Tissue Culture: Laboratory Procedures, John Wiley & Sons, Chichester, England (1996); Culture of Animal Cells, A Manual of Basic Techniques, 4 th Ed., Wiley-Liss (2000)).

The growth or culture media used in any of the culturing steps of the present invention, whether under aerobic or hypoxic conditions, may include serum, or be serum free. In one aspect, the media is Dulbecco's Modified Eagle Medium with 4.5 g/L glucose, alanyl-L-glutamine, Eq 2 mM, and nominally supplemented with 10% fetal bovine serum. In another aspect, the media is a serum free media and is Dulbecco's Modified Eagle Medium with 4.5 g/L glucose base medium with Glutamax®, supplemented with 0.5% serum albumin, 2 μg/ml heparin, 1 μg/ml recombinant basic FGF, 1 μg/ml soybean trypsin inhibitor, 1×ITS supplement (insulin-transferrin-selenium, Sigma Cat. No. I3146), 1:1000 diluted fatty acid supplement (Sigma Cat. No. 7050), and 1:1000 diluted cholesterol. Additionally, the same media can be used for both hypoxic and aerobic cultivation. In one aspect, the growth media is changed from serum based media to serum free media after seeding and the first week of growth.

Incubation conditions will be under appropriate conditions of pH, temperature, and gas (e.g., $O_2$, $CO_2$, etc) to maintain an hypoxic growth condition. In some embodiments, the three-dimensional cell culture can be suspended in the medium during the incubation period in order to maximize proliferative activity and generate factors that facilitate the desired biological activities of the fractions. In addition, the culture may be "fed" periodically to remove the spent media, depopulate released cells, and add new nutrient source. During the incubation period, the cultured cells grow linearly along and envelop the filaments of the three-dimensional scaffold before beginning to grow into the openings of the scaffold.

During incubation under hypoxic conditions, as compared to incubation under normal atmospheric oxygen concentrations of about 15-20%, thousands of genes are differentially expressed. Several genes have been found to be upregulated or downregulated in such compositions, most notably certain laminin species, collagen species and Wnt factors. In various aspects, the three dimensional ECM may be defined by the characteristic fingerprint or suite of cellular products produced by the cells due to growth in hypoxic condition as compared with growth under normal conditions. In the ECM compositions specifically exemplified herein, the three-dimensional tissues and surrounding media are characterized by expression and/or secretion of various factors.

The three dimensional tissues and compositions described herein have ECM that is present on the scaffold or framework. In some embodiments, the ECM includes various laminin and collagen types due to growth under hypoxic conditions and selection of cells grown on the support. The proportions of ECM proteins deposited can be manipulated or enhanced by selecting fibroblasts which elaborate the appropriate collagen type as well as growing the cells under hypoxic conditions in which expression of specific laminin and collagen species are upregulated or down-regulated.

Selection of fibroblasts can be accomplished in some aspects using monoclonal antibodies of an appropriate isotype or subclass that define particular collagen types. In other aspects, solid substrates such as magnetic beads may be used to select or eliminate cells that have bound antibody. Combination of these antibodies can be used to select (positively or negatively) the fibroblasts which express the desired collagen type. Alternatively, the stroma used to inoculate the framework can be a mixture of cells which synthesize the desired collagen types.

As discussed above, the ECM compositions described herein include various collagens. Accordingly, in one aspect of the present invention, the ECM composition including one or more embryonic proteins, includes upregulation of collagen species as compared with that produced in oxygen conditions of about 15-20% oxygen. In another aspect, the upregulated collagen species are type V alpha 1; IX alpha 1; IX alpha 2; VI alpha 2; VIII alpha 1; IV, alpha 5; VII alpha 1; XVIII alpha 1; and XII alpha 1.

In addition to various collagens, the ECM composition described herein include various laminins. Laminins are a family of glycoprotein heterotrimers composed of an alpha, beta, and gamma chain subunit joined together through a coiled-coil domain. To date, 5 alpha, 4 beta, and 3 gamma laminin chains have been identified that can combine to form 15 different isoforms. Within this structure are identifiable domains that possess binding activity towards other laminin and basal lamina molecules, and membrane-bound receptors. Domains VI, IVb, and IVa form globular structures, and domains V, IIIb, and IIIc (which contain cysteine-rich EGF-like elements) form rod-like structures. Domains I and II of the three chains participate in the formation of a triple-stranded coiled-coil structure (the long arm).

Laminin chains possess shared and unique functions and are expressed with specific temporal (developmental) and spatial (tissue-site specific) patterns. The laminin alpha-chains are considered to be the functionally important portion of the heterotrimers, as they exhibit tissue-specific distribution patterns and contain the major cell interaction sites. Vascular endothelium is known to express two laminin isoforms, with varied expression depending on the developmental stage, vessel type, and the activation state of the endothelium.

Accordingly, in one aspect of the present invention, the ECM composition including one or more embryonic proteins, includes upregulation or downregulation of various laminin species as compared with that produced in oxygen conditions of about 15-20% oxygen.

Laminin 8 is composed of alpha-4, beta-1, and gamma-1 laminin chains. The laminin alpha-4 chain is widely distributed both in adults and during development. In adults it can be identified in the basement membrane surrounding cardiac, skeletal, and smooth muscle fibers, and in lung alveolar septa. It is also known to exist in the endothelial basement membrane both in capillaries and larger vessels, and in the perineurial basement membrane of peripheral nerves, as well as in intersinusoidal spaces, large arteries, and smaller arterioles of bone marrow. Laminin 8 is a major laminin isoform in the vascular endothelium that is expressed and adhered to by platelets and is synthesized in 3T3-L1 adipocytes, with its level of synthesis shown to increase upon adipose conversion of the cells. Laminin 8 is thought to be the laminin isoform generally expressed in mesenchymal cell lineages to induce microvessels in connective tissues. Laminin 8 has also been identified in mouse bone marrow primary cell cultures, arteriolar walls, and intersinusoidal spaces where it is the major laminin isoform in the developing bone marrow. Due to its localization in adult bone marrow adjacent to hematopoietic cells, laminin isoforms containing the alpha-4 chain are likely to have biologically relevant interactions with developing hematopoietic cells.

Accordingly, in another aspect of the present invention, the ECM includes upregulation of laminin species, such as laminin 8. In another aspect, laminins produced by the three dimensional tissues of the present invention, includes at least laminin 8, which defines a characteristic or signature of the laminin proteins present in the composition.

The ECM compositions described herein can include various Wnt factors. Wnt family factors are signaling molecules having roles in a myriad of cellular pathways and cell-cell interaction processes. Wnt signaling has been implicated in tumorigenesis, early mesodermal patterning of the embryo, morphogenesis of the brain and kidneys, regulation of mammary gland proliferation, and Alzheimer's disease. Accordingly, in one aspect of the present invention, the ECM composition including one or more embryonic proteins, includes upregulation of Wnt species as compared with that produced in oxygen conditions of about 15-20% oxygen. In another aspect, the upregulated Wnt species are wnt 7a and wnt 11. In another aspect, Wnt factors produced by the three dimensional tissues of the present invention, include at least wnt7a, and wnt11, which defines a characteristic or signature of the Wnt proteins present in the composition.

The culturing methods described herein, including culture under hypoxic conditions, have also been shown to upregulate expression of various growth factors. Accordingly, the ECM compositions described herein can include various growth factors, such as a vascular endothelial growth factor (VEGF). As used herein, a VEGF in intended to include all known VEGF family members. VEGFs are a sub-family of growth factors, more specifically of platelet-derived growth factor family of cystine-knot growth factors. VEGFs have a well known role in both vasculogenesis and angiogenesis. Several VEGFs are known, including VEGF-A, which was formerly known as VEGF before the discovery of other VEGF species. Other VEGF species include placenta growth factor (PlGF), VEGF-B, VEGF-C and VEGF-D. Additionally, several isoforms of human VEGF are well known.

In accordance with the increased production of Wnt proteins as well as growth factors by culturing under hypoxic conditions as described herein, the present invention further provides a method of producing a Wnt protein and a vascular endothelial growth factor (VEGF). The method can include culturing cells under hypoxic conditions as described herein, on a three-dimensional surface in a suitable growth medium, to produce the Wnt protein and the VEGF. In an exemplary aspect, the Wnt species are wnt 7a and wnt 11 and the VEGF is VEGF-A. The proteins may be further processed or harvested as described further herein or by methods known in the art.

The ECM compositions of the present invention may include both soluble and non-soluble fractions or any portion thereof. It is to be understood that the compositions of the present invention may include either or both fractions, as well as any combination thereof. Additionally, individual components may be isolated from the fractions to be used individually or in combination with other isolates or known compositions.

Accordingly, in various aspects, ECM compositions produced using the methods of the present invention may be used directly or processed in various ways, the methods of which may be applicable to both the non-soluble and soluble fractions. The soluble fraction, including the cell-free supernatant and media, may be subject to lyophilization for preserving and/or concentrating the factors. Various biocompatible preservatives, cryoprotectives, and stabilizer agents may be used to preserve activity where required. Examples of biocompatible agents include, among others, glycerol, dimethyl sulfoxide, and trehalose. The lyophilizate may also have one or more excipients such as buffers, bulking agents, and tonicity modifiers. The freeze-dried media may be reconstituted by addition of a suitable solution or pharmaceutical diluent, as further described below.

In other aspects, the soluble fraction is dialyzed. Dialysis is one of the most commonly used techniques to separate sample components based on selective diffusion across a porous membrane. The pore size determines molecular-weight cutoff (MWCO) of the membrane that is characterized by the molecular-weight at which 90% of the solute is retained by the membrane. In certain aspects membranes with any pore size is contemplated depending on the desired cutoff. Typical cutoffs are 5,000 Daltons, 10,000 Daltons, 30,000 Daltons, and 100,000 Daltons, however all sizes are contemplated.

In some aspects, the soluble fraction may be processed by precipitating the active components (e.g., growth factors) in the media. Precipitation may use various procedures, such as salting out with ammonium sulfate or use of hydrophilic polymers, for example polyethylene glycol.

In other aspects, the soluble fraction is subject to filtration using various selective filters. Processing the soluble fraction by filtering is useful in concentrating the factors present in the fraction and also removing small molecules and solutes used in the soluble fraction. Filters with selectivity for specified molecular weights include <5000 Daltons, <10,000 Daltons, and <15,000 Daltons. Other filters may be used and the processed media assayed for therapeutic activity as described herein. Exemplary filters and concentrator system include those based on, among others, hollow fiber filters, filter disks, and filter probes (see, e.g., Amicon Stirred Ultrafiltration Cells).

In still other aspects, the soluble fraction is subject to chromatography to remove salts, impurities, or fractionate various components of the medium. Various chromatographic techniques may be employed, such as molecular sieving, ion exchange, reverse phase, and affinity chromatographic techniques. For processing conditioned medium without significant loss of bioactivity, mild chromatographic media may be used. Non-limiting examples include, among others, dextran, agarose, polyacrylamide based separation media (e.g., available under various tradenames, such as Sephadex, Sepharose, and Sephacryl).

In still other aspects, the conditioned media is formulated as liposomes. The growth factors may be introduced or encapsulated into the lumen of liposomes for delivery and for extending life time of the active factors. As known in the art, liposomes can be categorized into various types: multilamellar (MLV), stable plurilamellar (SPLV), small unilamellar (SUV) or large unilamellar (LUV) vesicles. Liposomes can be prepared from various lipid compounds, which may be synthetic or naturally occurring, including phosphatidyl ethers and esters, such as phosphotidylserine, phosphotidylcholine, phosphatidyl ethanolamine, phosphatidylinositol, dimyristoylphosphatidylcholine; steroids such as cholesterol; cerebrosides; sphingomyelin; glycerolipids; and other lipids (see, e.g., U.S. Pat. No. 5,833,948).

The soluble fraction may be used directly without additional additives, or prepared as pharmaceutical compositions with various pharmaceutically acceptable excipients, vehicles or carriers. A "pharmaceutical composition" refers to a form of the soluble and/or non-soluble fractions and at least one pharmaceutically acceptable vehicle, carrier, or excipient. For intradermal, subcutaneous or intramuscular administration, the compositions may be prepared in sterile suspension, solutions or emulsions of the ECM compositions in aqueous or oily vehicles. The compositions may also contain formulating agents, such as suspending, stabilizing or dispersing agents. Formulations for injection may be presented in unit dosage form, ampules in multidose containers, with or without preservatives. Alternatively, the compositions may be presented in powder form for reconstitution with a suitable vehicle including, by way of example and not limitation, sterile pyrogen free water, saline, buffer, or dextrose solution.

In other aspects, the three dimensional tissues are cryopreserved preparations, which are thawed prior to use. Pharmaceutically acceptable cryopreservatives include, among others, glycerol, saccharides, polyols, methylcellulose, and dimethyl sulfoxide. Saccharide agents include monosaccharides, disaccharides, and other oligosaccharides with glass transition temperature of the maximally freeze-concentrated solution (Tg) that is at least −60, −50, −40, −30, −20, −10, or 0° C. An exemplary saccharide for use in cryopreservation is trehalose.

In some aspects, the three dimensional tissues are treated to kill the cells prior to use. In some aspects, the ECM deposited on the scaffolds may be collected and processed for administration (see U.S. Pat. Nos. 5,830,708 and 6,280,284, incorporated herein by reference).

In some embodiments, the three dimensional tissue may be concentrated and washed with a pharmaceutically acceptable medium for administration. Various techniques for concentrating the compositions are available in the art, such as centrifugation or filtering. Examples include, dextran sedimentation and differential centrifugation. Formulation of the three dimensional tissues may also involve adjusting the ionic strength of the suspension to isotonicity (i.e., about 0.1 to 0.2) and to physiological pH (i.e., pH 6.8 to 7.5). The formulation may also contain lubricants or other excipients to aid in administration or stability of the cell suspension. These include, among others, saccharides (e.g., maltose) and organic polymers, such as polyethylene glycol and hyaluronic acid. Additional details for preparation of various formulations are described in U.S. Patent Publication No. 2002/0038152, incorporated herein by reference.

As discussed above, the ECM compositions of the present invention may be processed in a number of ways depending on the anticipated application and appropriate delivery or administration of the ECM composition. The terms "administration" or "administering" are defined to include an act of providing a compound or pharmaceutical composition of the invention to a subject in need of treatment. In some embodiments, the composition is administered topically on the skin.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

The ECM compositions of the present invention have a variety of applications including, but not limited to, promoting repair and/or regeneration of damaged cells or tissues, use in patches to promote tissue regeneration, use in tissue culture systems for culturing cells, such as stem cells, use in surface coatings used in association with implantable devices (e.g., pacemakers, stents, stent grafts, vascular prostheses, heart valves, shunts, drug delivery ports or catheters), promoting soft tissue repair, augmentation, and/or improvement of a skin surface, such as wrinkles, use as a biological anti-adhesion agent or as a biological vehicle for cell delivery or maintenance at a site of delivery.

Additionally, the ECM compositions derived from culturing cells as described in any method herein, may be used in any other application or method of the present invention. For example, the ECM compositions generated by culturing cells using the tissue culture system of the present invention may be used, for example, in the repair and/or regeneration of cells, use in patches to promote tissue regeneration, use in tissue culture systems for culturing cells, such as stem cells, use in surface coatings used in association with implantable devices (e.g., pacemakers, stents, stent grafts, vascular prostheses, heart valves, shunts, drug delivery ports or catheters), promoting soft tissue repair, augmentation, and/or improvement of a skin surface, such as wrinkles, use as a biological anti-adhesion agent or as a biological vehicle for cell delivery or maintenance at a site of delivery.

In various embodiments of any one of each or any of the above- or below-mentioned embodiments, methods for repair and/or regeneration of cells or tissue and promoting soft tissue repair are provided. One embodiment includes a method of repair and/or regeneration of cells by contacting cells to be repaired or regenerated with the ECM compositions of the present invention. The method may be used for repair and/or regeneration of a variety of cells as discussed herein, including osteochondral cells.

In some embodiments, formulations made with the ECM compositions may be used to treat aging skin of an individual. The skin of the individual may have loss of proteostasis, skin wounds, hyperpigmentation, loose or sagging skin, deep wrinkles, and/or fine lines. In some embodiments, the formulation for treating aging skin comprises ECM compositions made by the methods described herein. In some embodiments, the formulation for treating aging skin further comprises botanicals. In some embodiments, the formulation for treating aging skin further comprises marine extracts. In some embodiments, the formulation for treating aging skin further comprises peptides.

In one aspect, the method contemplates repair of osteochondral defects. As used herein, "osteochondral cells" refers to cells which belong to either the chondrogenic or osteogenic lineage or which can undergo differentiation into either the chondrogenic or osteogenic lineage, depending on the environmental signals. This potential can be tested in vitro or in vivo by known techniques. Thus, in one aspect, the ECM compositions of the present invention are used to repair and/or regenerate, chondrogenic cells, for example, cells which are capable of producing cartilage or cells which themselves differentiate into cells producing cartilage, including chondrocytes and cells which themselves differentiate into chondrocytes (e.g., chondrocyte precursor cells). Thus, in another aspect, the compositions of the present invention are useful in repair and/or regeneration of connective tissue. As used herein, "connective tissue" refers to any of a number of structural tissues in the body of a mammal including but not limited to bone, cartilage, ligament, tendon, meniscus, dermis, hyperdermis, muscle, fatty tissue, joint capsule.

The ECM compositions of the present invention may be used for treating defects or injury on the skin. The composition may be used for improving the quality of the skin on the individual. In some embodiments, the composition is used on the skin to improve the aesthetic appearance of the skin. In some embodiments, the composition leads to healing of the skin.

As discussed above, growth factors or other biological agents which induce or stimulate growth of particular cells may be included in the ECM compositions of the present invention. The type of growth factors will be dependent on the cell-type and application for which the composition is intended. For example, in the case of osteochondral cells, additional bioactive agents may be present such as cellular growth factors (e.g., TGF-0), substances that stimulate chondrogenesis (e.g., BMPs that stimulate cartilage formation such as BMP-2, BMP-12 and BMP-13), factors that stimulate migration of stromal cells to the scaffold, factors that stimulate matrix deposition, anti-inflammatories (e.g., non-steroidal anti-inflammatories), immunosuppressants (e.g., cyclosporin). Other proteins may also be included, such as other growth factors such as platelet derived growth factors (PDGF), insulin-like growth factors (IGF), fibroblast growth factors (FGF), epidermal growth factor (EGF), human endothelial cell growth factor (ECGF), granulocyte macrophage colony stimulating factor (GM-CSF), vascular endothelial growth factor (VEGF), cartilage derived morphogenetic protein (CDMP), other bone morphogenetic proteins such as OP-1, OP-2, BMP3, BMP4, BMP9, BMP11, BMP14, DPP, Vg-1, 60A, and Vgr-1, collagens, elastic fibers, reticular fibers, glycoproteins or glycosaminoglycans, such as heparin sulfate, chondroitin-4-sulfate, chondroitin-6-sulfate, dermatan sulfate, keratin sulfate, etc. For example, growth factors such as TGF-13, with ascorbate, have been found to trigger chondrocyte differentiation and cartilage formation by chondrocytes. In addition, hyaluronic acid is a good substrate for the attachment of chondrocytes and other stromal cells and can be incorporated as part of the scaffold or coated onto the scaffold.

Additionally, other factors which influence the growth and/or activity of particular cells may also be used. For example, in the case of chondrocytes, a factor such as a chondroitinase which stimulates cartilage production by chondrocytes can be added to the matrix in order to maintain chondrocytes in a hypertrophic state as described in U.S. Patent Application No. 2002/0122790, incorporated herein by reference. In some embodiments, the methods include the presence of polysulphated alginates or other polysulphated polysaccharides such as polysulphated cyclodextrin and/or polysulphated inulin, or other components capable of stimulating production of ECM of connective tissue cells as described in International Patent Publication No. WO 2005/054446, incorporated herein by reference.

The cell or tissue to be repaired and/or regenerated may be contacted in vivo or in vitro by any of the methods described herein. For example, the ECM compositions may be applied topically onto the skin of the subject. In another aspect, the tissue or cells to be repaired and/or regenerated may be harvested from the subject and cultured in vitro and subsequently implanted or administered to the subject using known surgical techniques.

As discussed above, the ECM compositions of the present invention may be processed in a variety of ways. Accordingly, in one embodiment, the present invention includes a tissue culture system. In various aspects, the culture system is composed of the ECM compositions described herein. The ECM compositions of the present invention may be incorporated into the tissue culture system in a variety of ways. For example, compositions may be incorporated as coatings, by impregnating three-dimensional scaffold materials as described herein, or as additives to media for culturing cells. Accordingly, in one aspect, the culture system can include three-dimensional support materials impregnated with any of the ECM compositions described herein, such as growth factors or embryonic proteins.

The ECM compositions described herein may serve as a support or three-dimensional support for the growth of various cell types. Any cell type capable of cell culture is contemplated. In one aspect, the culture system can be used to support the growth of stem cells. In another aspect, the stem cells are embryonic stem cells, mesenchymal stem cells or neuronal stem cells.

The tissue culture system may be used for generating additional ECM compositions, such as implantable tissue. Accordingly, culturing of cells using the tissue culture system of the present invention may be performed in vivo or in vitro. For example, the tissue culture system of the present invention may be used to generate ECM compositions for injection or implantation into a subject. The ECM compositions generated by the tissue culture system may be processed and used in any method described herein.

The ECM compositions of the present invention may be used as a biological vehicle for cell delivery. As described herein, the ECM compositions may include both soluble and/or non-soluble fractions. As such, in another embodiment of the present invention, a biological vehicle for cell delivery or maintenance at a site of delivery including the ECM compositions of the present invention, is described. The ECM compositions of the present invention, including cells and three-dimensional tissue compositions, may be used to promote and/or support growth of cells in vivo. The vehicle can be used in any appropriate application, for example to support injections of cells, such as stem cells, into damaged heart muscle or for tendon and ligament repair as described above.

Appropriate cell compositions (e.g., isolated ECM cells of the present invention and/or additional biological agents) can be administered before, after or during the ECM compositions are administered. For example, the cells can be seeded into the site of administration, defect, and/or implantation before the culture system or biological delivery vehicle is implanted into the subject. Alternatively, the appropriate cell compositions can be administered after (e.g., by injection into the site). The cells act therein to induce tissue regeneration and/or cell repair.

ECM compositions have been described for promoting angiogenesis in organs and tissues by administering such compositions to promote endothelialization and vascularization in the heart and related tissues. Accordingly, in yet another embodiment, the present invention applying the ECM composition topically. The preparation and use of ECM compositions grown under normal oxygen conditions is described in U.S. Patent Application No. 2004/0219134 incorporated herein by reference.

In some embodiments, various implantable devices and tissue regeneration patches including the ECM compositions described herein which allow for benefits, such as tissue ingrowth are provided. As discussed herein, the ECM compositions may serve as coatings on medical devices, such as patches or other implantable devices. In some embodiments, such devices are useful for wound repair.

A variety of techniques are known in the art for applying biological coatings to medical device surfaces that may be utilized with the present invention. For example, ECM compositions may be coated using photoactive crosslinkers allowing for permanent covalent bonding to device surfaces upon activation of the crosslinker by applying ultraviolet radiation. An exemplary crosslinker is TriLite™ crosslinker, which has been shown to be non-cytotoxic, non-irritating to biological tissue and non-sensitizing. ECM materials may be unseparated or separated into individual components, such as human collagens, hyaluronic acid (HA), fibronectin, and the like before coating or incorporation into various implantable devices. Further, additional growth factors and such may be incorporated to allow for beneficial implantation characteristics, such as improved cell infiltration.

In various related embodiments, methods and devices applicable in cosmetic and cosmeceutical applications, such as, but not limited to anti-aging, anti-wrinkle, skin fillers, moisturizers, pigmentation augmentation, skin firming, and the like, are provided. Accordingly, in one embodiment, the present invention includes a method for improvement of a skin surface in a subject including administering to the subject at the site of a wrinkle, the ECM compositions described herein. In a related embodiment, the present invention includes a method for soft tissue repair or augmentation in a subject including administering to the subject at the site of a wrinkle, the ECM compositions described herein. In various cosmetic applications, the compositions may be formulated as appropriate, such as topical formulations. In some embodiments, ECM compositions formulated as topicals have been shown to be effective in various skin aesthetics applications, such as anti-wrinkle, anti-aging applications as well as an adjunct to ablative laser surgery. Several beneficial characteristics of ECM containing topicals have been shown. Such benefits include 1) facilitating re-epithelization following resurfacing; 2) reduction of non-ablative and ablative fractional laser resurfacing symptoms (e.g., erythema, edema, crusting, and sensorial discomfort); 3) generating smooth, even textured skin; 4) generating skin moisturization; 5) reducing appearance of fine lines/wrinkles; 6) increasing skin firmness and suppleness; 7) reducing skin dyspigmentation; and 8) reducing red, blotchy skin.

The compositions of the present invention may be prepared as known in the art, however employing the innovative culture methods described herein (e.g., culture under hypoxic conditions). The preparation and use of ECM compositions created under normal oxygen culture conditions for the repair and/or regeneration of cells, improvement of skin surfaces, and soft tissue repair are described in U.S. Pat. Nos. 5,830,708, 6,284,284, U.S. Patent Application No. 2002/0019339 and U.S. Patent Application No. 2002/0038152, all incorporated herein by reference.

The compositions or active components used herein, will generally be used in an amount effective to treat or prevent the particular defect, skin condition and/or disease being treated. The compositions may be administered therapeutically to achieve therapeutic benefit or prophylactically to achieve prophylactic benefit. Therapeutic benefit includes the eradication or amelioration of an underlying defect, skin condition, disorder and/or disease being treated. Therapeutic benefit also includes halting or slowing the progression of the defect, skin condition, disorder and/or disease, regardless of whether improvement is realized.

The amount of the composition administered will depend upon a variety of factors, including, for example, the type of composition, the particular indication being treated, the mode of administration, whether the desired benefit is prophylactic or therapeutic, the severity of the indication being treated and the age and weight of the patient, and effectiveness of the dosage form. Determination of an effective dosage is well within the capabilities of those skilled in the art.

Initial dosages may be estimated initially from in vitro assays. Initial dosages can also be estimated from in vivo data, such as animal models. Animals models useful for testing the efficacy of compositions for enhancing hair growth include, among others, rodents, primates, and other mammals. The skilled artisans can determine dosages suitable for human administration by extrapolation from the in vitro and animal data.

Dosage amounts will depend upon, among other factors, the activity of the conditioned media, the mode of administration, the condition being treated, and various factors discussed above. Dosage amount and interval may be adjusted individually to provide levels sufficient to the maintain the therapeutic or prophylactic effect.

Presented below are examples discussing generation of ECM compositions contemplated for the discussed applications. The following examples are provided to further illustrate the embodiments of the present invention, but are not intended to limit the scope of the invention. While they are typical of those that might be used, other procedures, methodologies, or techniques known to those skilled in the art may alternatively be used.

Methods of Making a Composition

In some aspects, a method of producing a composition for improvement of a tissue in a subject is provided. The method comprises culturing fibroblast cells under hypoxic conditions on microcarrier beads or a three dimensional surface in a suitable growth medium, under 1-5% oxygen, thereby producing multipotent stem cells, wherein the multipotent stem cells produce and secrete into a growth medium a composition that promotes repair and regeneration of damaged tissue when administered to the region of tissue in need of repair in the subject and collecting the growth medium, thereby producing the composition. In some embodiments, additives to the composition comprise at least one botanical, at least one extract, at least one peptide, at least one protein and/or at least one marine extract. In some embodiments, the culturing is performed on microcarrier beads or a three dimensional surface in a suitable growth medium. In some embodiments, the culturing is performed for at least two weeks. In some embodiments, the growth medium is collected after two weeks. In some embodiments, the method further comprises adding a seed extract to the composition. In some embodiments, the method further comprises adding a marine extract to the composition. In some embodiments, the method further comprises adding a bacterial ferment to the composition. In some embodiments, the growth medium further comprises stem cell factors. In some embodiments, the growth medium further comprises cytokines. In some embodiments, the growth medium further comprises at least one matrix protein. In some embodiments, the at least one peptide comprises dimer tripeptide 43 and/or trifluoroacetyl tripeptide-2. In some embodiments, the subject is in need of tissue repair. In some embodiments, the subject has fine and or deep wrinkles. In some embodiments, the subject exhibits tactile and/or skin roughness of the tissue. In some embodiments, the subject has hyperpigmentation. In some embodiments, the subject has photodamage. In some embodiments, the subject lacks evenness in pigmentation and/or skin tone. In some embodiments, the subject has a skin coloring on the Fitzpatrick scale of 1, 2, 3, 4 or 5.

Compositions

A composition made by the method of any one of the embodiments of any one of each or any of the above- or below-mentioned embodiments for use in treating a subject is provided.

In some embodiments, the composition further comprises at least one botanical.

In some embodiments, the composition further comprises at least one extract.

In some embodiments, the composition further comprises at least one peptide.

In some embodiments, the composition further comprises a seed extract.

In some embodiments, the composition further comprises a marine extract.

In some embodiments, the composition further comprises a bacterial ferment.

In some embodiments, the composition further comprises stem cell factors.

In some embodiments, the composition further comprises cytokines.

In some embodiments, the composition further comprises at least one matrix protein.

In some embodiments, the at least one peptide comprises dimer tripeptide 43 and/or trifluoroacetyl tripeptide-2.

In some embodiments, a composition is provided comprising: growth medium, wherein the growth medium is collected from multipotent stem cells produced under hypoxic conditions; at least one botanical, at least one extract, and at least one peptide.

In some embodiments, the composition is odorless.

In some embodiments, the composition is clear.

Methods of Treatment

In some embodiments, a method of improving the appearance of an individual is provided, the method comprising topically applying the composition of any one of embodiments herein, onto a tissue of a subject to thereby improve the aesthetic quality of the tissue.

In some embodiments, the subject has fine or deep wrinkles.

In some embodiments, the subject has tactile and/or skin roughness of the tissue.

In some embodiments, the subject has loose or sagging skin.

In some embodiments, the method improves roughness of skin.

In some embodiments, the method restores volume moisture to the tissue.

In some embodiments, the method results in reduced inflammatory response of the tissue.

In some embodiments, the subject is in need of tissue repair.

In some embodiments, the subject is suffering from a burn wound.

In some embodiments, the method leads to healing of the tissue.

In some embodiments, skin is protected from free radical damage.

In some embodiments, the composition supports epidermal cell-cell adhesion.

In some embodiments, the composition supports a dermal epidermal junction.

In some embodiments, the composition supports stem cells function and proliferation.

In some embodiments, the composition supports intercellular communication.

In some embodiments, the composition supports cellular recycling and protein homeostasis.

In some embodiments, the composition prevents cellular senescence.

In some embodiments, the composition supports collagen, elastin and ECM components.

In some embodiments, the composition supports heparan sulfate and proteoglycans.

In some embodiments, the composition increases expression of stemness biomarkers.

In some embodiments, the composition provides comprehensive skin rejuvenation at the epidermis, dermal-epidermal junction and the dermis.

In some embodiments, application of the composition increases gene expression of proliferation and myofibroblast markers.

In some embodiments, application of the composition increases expression of stemness biomarkers.

In some embodiments, application of the composition improves the appearance of fine lines and deep wrinkles.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for treating skin defects comprising topically applying a topical composition onto a subject's skin wherein the topical composition comprises:
   (i) a growth medium obtained from culturing human fibroblast cells under hypoxic conditions on microcarrier beads or a three dimensional surface in a suitable cell culture medium, under 1-5% oxygen and the growth medium is present within a range of about 0.1% to about 30% by weight of the topical composition;
   (ii) at least one botanical or botanical extract present within a range of about 0.5% to about 2.0% by weight of the topical composition;
   (iii) about 0.0001% to about 0.001% by weight of the topical composition of a combination of dimer tripeptide 43 and trifluoroacetyl tripeptide-2;
   (iv) at least one seed extract present within a range of about 0.5% to about 2% by weight of the topical composition;
   (v) at least one marine extract present within a range of about 0.01% to about 0.1% by weight of the topical composition; and
   (vi) at least one bacterial ferment present within a range of about 0.5% to about 3.0% by weight of the topical composition.

2. The method of claim 1, wherein the skin defect is fine or deep wrinkles.

3. The method of claim 1, wherein the skin defect is tactile roughness of the tissue.

4. The method of claim 1, wherein the skin defect is loose or sagging skin.

5. The method of claim 1, wherein the method improves roughness of skin.

6. The method of claim 1, wherein the method restores volume moisture to the tissue.

7. The method of claim 1, wherein the method results in reduced inflammatory response of the tissue.

8. The method of claim 1, wherein the skin defect is a defect of a subject's skin and the composition protects the skin from free radical damage.

9. The method of claim 1, wherein the growth medium comprises stem cell factors.

10. The method of claim 1 wherein the growth medium comprises at least one cytokine.

11. The method of claim 1 wherein the human fibroblast cells are obtained from human neonatal foreskin.

12. The method of claim 1 wherein the growth medium is obtained from culturing human fibroblast cells under hypoxic conditions on microcarrier beads comprising dextran.

* * * * *